(12) United States Patent
Deshmukh et al.

(10) Patent No.: US 9,884,022 B2
(45) Date of Patent: Feb. 6, 2018

(54) CONTROLLED RELEASE PHARMACEUTICAL COMPOSITIONS OF TAPENTADOL

(75) Inventors: Ashish Ashokrao Deshmukh, Pune (IN); Pravin Meghrajji Bhutada, Pune (IN); Sajeev Chandran, Pune (IN); Shirishkumar Kulkarni, Pune (IN)

(73) Assignee: LUPIN LIMITED, Mumbai (IN)

( * ) Notice: Subject to any disclaimer, the term of this patent is extended or adjusted under 35 U.S.C. 154(b) by 227 days.

(21) Appl. No.: 13/638,239

(22) PCT Filed: Feb. 7, 2011

(86) PCT No.: PCT/IB2011/000196
§ 371 (c)(1),
(2), (4) Date: Sep. 28, 2012

(87) PCT Pub. No.: WO2011/124953
PCT Pub. Date: Oct. 13, 2011

(65) Prior Publication Data
US 2013/0022654 A1    Jan. 24, 2013

(30) Foreign Application Priority Data

Apr. 7, 2010  (IN) .............................. 393/KOL/2010

(51) Int. Cl.
| | | |
|---|---|---|
| *A61K 31/137* | (2006.01) | |
| *A61K 9/00* | (2006.01) | |
| *A61P 25/00* | (2006.01) | |
| *C07C 215/54* | (2006.01) | |
| *A61K 9/24* | (2006.01) | |
| *A61K 9/16* | (2006.01) | |
| *A61K 9/20* | (2006.01) | |
| *A61K 9/50* | (2006.01) | |
| *A61K 45/06* | (2006.01) | |

(52) U.S. Cl.
CPC ............ *A61K 9/209* (2013.01); *A61K 9/0004* (2013.01); *A61K 9/0065* (2013.01); *A61K 9/1617* (2013.01); *A61K 9/1635* (2013.01); *A61K 9/1652* (2013.01); *A61K 9/1676* (2013.01); *A61K 9/2054* (2013.01); *A61K 9/2077* (2013.01); *A61K 9/5026* (2013.01); *A61K 9/5042* (2013.01); *A61K 31/137* (2013.01); *A61K 45/06* (2013.01)

(58) Field of Classification Search
CPC .. A61K 9/0004; A61K 9/1652; A61K 9/0065; A61K 45/06; A61K 9/1617; A61K 9/1635; A61K 31/137; A61K 9/1676; A61K 9/2054; A61K 9/2077; A61K 9/209; A61K 9/5026; A61K 9/5042
See application file for complete search history.

(56) References Cited

U.S. PATENT DOCUMENTS

| | | |
|---|---|---|
| RE39,593 E | 4/2007 | Buschmann et al. |
| 2005/0058706 A1 | 3/2005 | Bartholomaeus et al. |
| 2009/0011019 A1* | 1/2009 | Jahagirdar ........... A61K 9/0065 424/472 |
| 2009/0099138 A1 | 4/2009 | Schiene et al. |
| 2011/0195989 A1* | 8/2011 | Rudnic et al. ................ 514/282 |

FOREIGN PATENT DOCUMENTS

| | | | | |
|---|---|---|---|---|
| WO | WO9917745 | * | 4/1999 | ............... A61K 9/20 |
| WO | WO 03/035053 | | 3/2003 | |
| WO | WO 2006/002886 | | 1/2006 | |
| WO | WO 2009/067703 | | 5/2009 | |
| WO | WO 2009/092601 | | 7/2009 | |

OTHER PUBLICATIONS

International Search Report and Written Opinion from International Application No. PCT/IB2011/000196 dated Feb. 20, 2012.

* cited by examiner

*Primary Examiner* — Suzanne Ziska
*Assistant Examiner* — Thurman Wheeler
(74) *Attorney, Agent, or Firm* — Merchant & Gould P.C.

(57) ABSTRACT

A once daily controlled release pharmaceutical compositions comprising tapentadol, wherein preferably the mean $T_{max}$ of tapentadol is reached after 10 hours of administration of the composition. The composition comprises tapentadol, such that it maintains serum concentration of tapentadol of at least about 20 ng/ml for at least about 17 hours after oral administration of the composition. According to one embodiment the controlled release pharmaceutical composition comprises tapentadol, which is gastroretentive.

7 Claims, 2 Drawing Sheets

CONTROLLED RELEASE PHARMACEUTICAL COMPOSITIONS OF TAPENTADOL

This application is a National Stage Application of PCT/IB2011/00019, filed 7 Feb. 2011, which claims benefit of Serial No. 393/KOL/2010, filed 7 Apr. 2010 in India and which applications are incorporated herein by reference. To the extent appropriate, a claim of priority is made to each of the above disclosed applications.

FIELD OF THE INVENTION

The present invention relates to once daily controlled release pharmaceutical compositions comprising tapentadol, wherein preferably the mean $T_{max}$ of tapentadol is reached after 10 hours of administration of the composition.

BACKGROUND OF THE INVENTION

Tapentadol is both μ-opioid receptor agonist and norephinephrine (NE) reuptake inhibitor. Chemically, tapentadol is 3-(3-dimethylamino-1-ethyl-2-methyl-propyl) phenol. US RE39,593 discloses tapentadol as an analgesic composition and can be administered orally.

Conventional compositions (i.e. immediate release compositions) for oral administration of tapentadol lead to rapid release of the active ingredient in the gastrointestinal tract resulting in quick onset of action, but at the same time, a subsequent rapid reduction in the action is observed due to short half life (4 hrs) of tapentadol. The immediate release tablets comprising tapentadol marketed by Ortho McNeil Janssen under the brand name of Nucynta® in various strengths i.e. 50 mg, 75 mg, 100 mg is thus required to be administered 4-6 times a day (i.e. at every 4-6 hours), to ensure an adequately high concentration of the active ingredient in vivo for perceptible pain relief. If adequate pain relief is not attained with the first dose, the second dose may be administered as soon as one hour after the first dose. The maximum recommended daily dose is 700 mg on the first day and 600 mg on subsequent days. Combinations of tapentadol with other active ingredients such as analgesics have also been prepared.

US 2009/0099138 by Kalus et al., discloses a combination of tapentadol and one or more non-steroidal anti-inflammatory drugs (NSAIDs).

WO 2009067703 by Ramesh Sesha discloses pharmaceutical compositions comprising slow release tapentadol hydrochloride in combination with a second analgesic.

US 2005/0058706 by Johannes Bartholomaeus et al., discloses a slow-release pharmaceutical composition, containing tapentadol or a pharmaceutically acceptable salt thereof in a matrix wherein a peak serum level of the active ingredient is obtained in vivo within 2 to 10 hrs after administration of the composition. It also discloses simulation studies with repeated administration of the pharmaceutical composition at 12 hourly intervals, which showed that, serum levels are achieved and do not fall below 20 ng/ml, so good analgesic efficacy is ensured by twice daily administration.

Frequent dosing easily leads to errors in administration as well undesirable variations in concentration in the serum which are detrimental to patient compliance and the therapeutic benefit, particularly when treating chronically painful conditions. Therefore, controlled release compositions are desirable that maintains the therapeutic serum concentration of tapentadol for an extended period of time upon administration.

A controlled release pharmaceutical composition have now been developed comprising tapentadol for once-daily administration which ensures better patient compliance, wherein preferably the mean $T_{max}$ of tapentadol is reached after 10 hours of administration of the composition.

SUMMARY OF THE INVENTION

One embodiment relates to once daily controlled release pharmaceutical composition comprising tapentadol, wherein preferably the mean $T_{max}$ of tapentadol is reached after 10 hours of administration of the composition.

Another embodiment relates to once daily controlled release pharmaceutical composition comprising tapentadol, wherein the composition maintains serum concentration of tapentadol at least about 10 ng/ml for at least about 14 hours, preferably for at least about 17 hours, more preferably for about 24 hours after administration of the composition, such that preferably the mean $T_{max}$ of tapentadol is reached after 10 hours of administration of the composition. Preferably, the serum concentration of tapentadol is maintained at least about 20 ng/ml for at least about 17 hours, preferably for upto about 24 hours after oral administration of the composition.

Further, embodiment relates to once daily controlled release pharmaceutical composition comprising tapentadol, wherein the pharmaceutical composition is gastroretentive. The composition may comprise an immediate release component and/or a controlled release component. The controlled release component may be gastroretentive or a combination of gastroretentive and delayed controlled release component. The delayed release and/or controlled release component may be osmotic and/or bioadhesive.

Another embodiment relates to once daily controlled release pharmaceutical composition comprising tapentadol, wherein the composition is a multi-layered composition. The multi-layered composition may comprise immediate release component and/or controlled release component. The controlled release component may be gastroretentive and/or comprises a delayed controlled release component. The delayed controlled release component may be osmotic or bioadhesive.

Another embodiment relates to once daily controlled release pharmaceutical composition comprising tapentadol, wherein the pharmaceutical composition is osmotic. The controlled release osmotic composition may be gastroretentive or bioadhesive.

Another embodiment relates to once daily controlled release pharmaceutical composition comprising tapentadol, wherein the pharmaceutical composition is bioadhesive. The bioadhesive composition may comprise immediate release component and/or controlled release component. The controlled release component may be bioadhesive and/or comprises a delayed controlled release component.

Another embodiment relates to a process for preparing such once daily controlled release pharmaceutical compositions comprising tapentadol and their uses.

Yet another embodiment relates to once daily controlled release pharmaceutical composition comprising tapentadol and one or more other active ingredient preferably a NSAID. The composition may comprise immediate release component and/or a controlled release component. The controlled release component may be gastro retentive, bioadhesive, osmotic, a delayed controlled release component or combinations thereof. The immediate release component may comprise tapentadol and/or one or more NSAID such as meloxicam or combinations thereof.

DETAILED DESCRIPTION OF THE INVENTION

Figure 1:
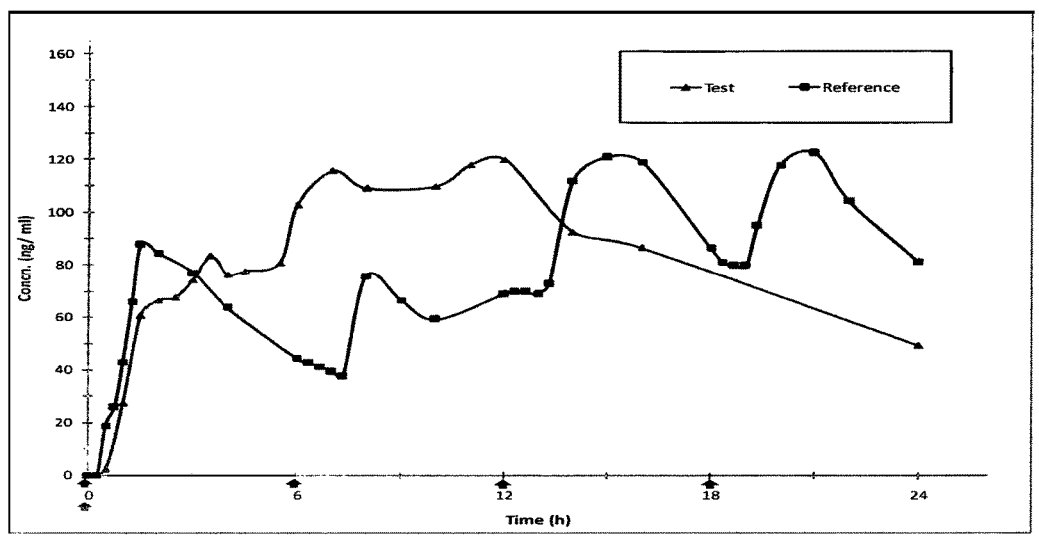
FIG. 1 is the serum concentration of tapentadol of Test (Example 19) administered QD and reference tapentadol IR tablet administered QID.
Figure 2:
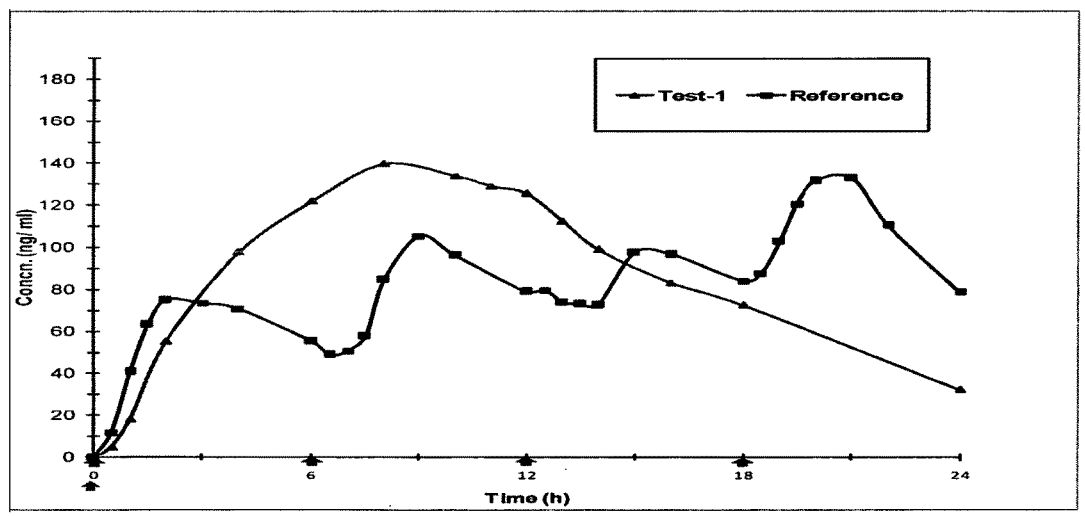
FIG. 2 is the serum concentration curve of tapentadol of Test 1 (example 20) administered once daily (QD) and reference (Nucynta®) administered QID.
Figure 3:
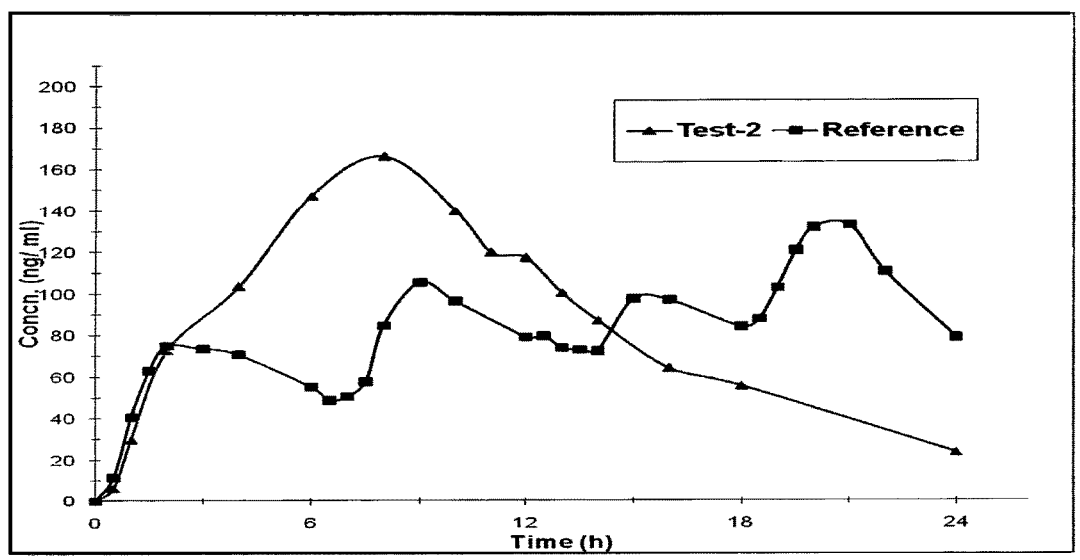
FIG. 3 is the serum concentration curve of tapentadol of Test 2 (example 21) administered once daily (QD) and reference (Nucynta®) administered QID.

One embodiment relates to once daily controlled release pharmaceutical compositions comprising tapentadol, wherein preferably the mean $T_{max}$ of tapentadol is reached after 10 hours of administration of the composition.

In another embodiment once daily controlled release pharmaceutical composition comprising tapentadol maintains serum concentration of tapentadol at least about 10 ng/ml for at least about 14 hours, preferably for at least about 17 hours, more preferably for about 24 hours after administration of the composition, such that preferably the mean $T_{max}$ of tapentadol is reached after 10 hours of administration of the composition. Preferably, the serum concentration is maintained at least about 20 ng/ml for at least about 17 hours after administration of the composition.

The term tapentadol includes various forms of tapentadol such as pharmaceutically acceptable salt(s), hydrate(s), solvate(s), polymorph(s), isomer(s), stereoisomer(s), enantiomer(s), racemate(s), ester(s), prodrug(s), derivative(s), analogou(s), metabolite(s) and complex(s) thereof.

The term "pharmaceutically acceptable salt" means a salt which is acceptable for administration to a patient, such as a mammal (e.g., salts having acceptable mammalian safety for a given dosage regime). Such salts can be derived from pharmaceutically acceptable inorganic or organic bases and from pharmaceutically acceptable inorganic or organic acids.

The active ingredient, active agent and drug herein can be interchangeably used.

The maximum recommended daily dose for tapentadol is 700 mg on the first day and 600 mg on subsequent days. The exact dose of active ingredient and the particular composition to be administered depend on a number of factors, e.g. the condition to be treated, the desired duration of the treatment and the rate of release of the active ingredient.

The active ingredient may be present from 1 to 90% w/w of the total composition.

In an embodiment the once daily controlled release pharmaceutical composition comprising tapentadol, may comprise an immediate release component and/or a controlled release component.

"Immediate release" means that releases substantially faster than controlled release or delayed release. About 5 to about 10% w/w of the total amount of tapentadol in the composition is released in vitro within about 30 minutes from the beginning of the dissolution, when measured under US Pharmacopoeia (USP) conditions in 0.1N HCl at 37° C. in a type II dissolution apparatus.

As used herein, "controlled release" means that the release of the active ingredient is substantially slower than immediate release. Examples of such controlled release include sustained release, slow release, prolonged release, delayed release, pulsatile release, extended release, timed release etc., which terms are generally known in the art and to the extent they mean a release other than an immediate release. Controlled release may be achieved by various technologies such as reservoir, matrix, osmotic, gastroretention, bioadhesion, complexation, conjugation etc.

Composition includes, without limitation, tablets, capsules, caplets, powders, pellets, granules, liquid dispersions, beads, etc. In some aspects, powders, pellets, and granules may be coated with a suitable polymer or a conventional coating material to achieve, for example, greater stability in the gastrointestinal tract, or to achieve the desired rate of release. Moreover, capsules containing a powder, pellets, or granules may be further coated. Tablets may be minitablets, multi-layered tablets, coated or uncoated tablets, tablet in tablet etc. those are known in art. It may also include kits. These compositions can be administered orally.

Component used herein means substantially entire or a part of a composition which includes powder, particles, granules, pellets, microspheres, tablets, minitablets, capsules, caplets, or a mixture thereof, or several such units formulated into a capsule or a tablet; as a matrix in a tablet; as a layer, that can be incorporated in a multilayer tablet; as a coating layer in a multicoated tablet or pellet. As used herein, the term "substantially entire or a part" refers to the nearly entire or a part of the composition that may be varied from 0.1% to 99.9% of the composition.

The immediate release component may be present as pharmaceutical immediate release unit(s) like for example immediate release powder, particles, granules, pellets, microspheres, tablets, minitablets, capsules, caplets, or a mixture thereof, or several such units formulated into a capsule or a tablet; as an immediate release matrix in a tablet; as an immediate release layer, that can be incorporated in a multilayer tablet; as an immediate release coating layer in a multicoated tablet or pellet. The immediate release component comprises about 4 to 12% of the tapentadol by weight of the total weight of tapentadol in the composition.

The controlled release component may be present as pharmaceutical controlled release unit(s) such as, for example prolonged release powder, particles, granules, pellets, microspheres, tablets, minitablets, capsules, caplets, or a mixture thereof, or several such units formulated into a capsule or a tablet; as a prolonged release layer, that can be incorporated in a multilayer tablet; as a prolonged release core or a prolonged release coating layer in a multicoated tablet; as prolonged release pellets within a disintegrating tablet. The controlled release component comprises about 10 to 90% of tapentadol by weight of total weight of tapentadol in the composition, preferably about 15 to 80% of tapentadol and more preferably about 18 to 65% of tapentadol by weight of total weight of tapentadol in the composition.

The term "core" as used herein may be a part of the composition surrounded by at least a part of the coating or layer. The core can be homogenous or have an internal structure comprising powder, particles, granules, pellets, tablets, minitablets, capsules, caplets, or a mixture thereof, comprising active ingredient(s) or carriers/substrates or a mixture thereof. Core may be prepared by addition of excipients, binder, disintegrant, lubricant and so on, as would be understood by one of ordinary skill in the art. Inert core used herein may be the part of the composition surrounded by at least a part of the coating or layer, which does not comprises active ingredient.

The terms "gastric retention" "gastro retention" or "gastroretentive" refers to the pharmaceutical composition, which is capable of being retained in the upper part of the gastrointestinal tract (GIT) of a subject for a prolonged period of time for e.g. for several hours to about 24 hours, usually up to about 12 hours, and often between about 3 to 18 hours, and preferably about 6 hours.

The term "$T_{max}$" refers to the time following ingestion when maximum serum concentration of active ingredient following the ingestion of a composition comprising the active ingredient is reached.

The term "AUC" as used herein means "area under the curve" in a plot of concentration of active ingredient in serum versus time from ingestion. AUC is usually given for the time interval zero to any time 't' post drug administration or extrapolated to infinity. AUC zero to infinity is estimated based on mathematical approaches using limited number of concentration measurements.

As used herein, "%" refers to the weight percent of a substance as it relates to the overall composition unless otherwise indicated.

The term "comprising", which is synonymous with "including", "containing", or "characterized by" here is defined as being inclusive or open-ended, and does not exclude additional, unrecited elements or method steps, unless the context clearly requires otherwise.

The once daily controlled release pharmaceutical composition comprises tapentadol and one or more pharmaceutically acceptable excipient(s) which includes release controlling agents, and may optionally contain binders, diluents, lubricants, glidants and plasticizers etc. The amount of excipient employed will depend upon the quantity of active ingredient to be used. One excipient can perform more than one function.

Release controlling agents are defined as hydrophilic or hydrophobic agents, which can be polymeric or non-polymeric and which are capable of controlling the rate or release of the active agent(s). The release controlling agents may be natural, semi-synthetic and synthetic agents or mixtures thereof. The release controlling agent can be used from about 1 to about 70% of the total composition.

The hydrophobic release controlling agents comprises but are not limited to hydrogenated vegetable oil, but other suitable agents include purified grades of beeswax; fatty acids; long chain fatty alcohols, such as cetyl alcohol, myristyl alcohol, and stearyl alcohol; glycerides such as glyceryl esters of fatty acids like glyceryl monostearate, glyceryl distearate, glyceryl esters of hydrogenated castor oil and the like; oils such as mineral oil and the like, or acetylated glycerides; ethyl cellulose, stearic acid, paraffin, carnauba wax, talc; and the stearate salt(s) such as calcium, magnesium, zinc and other materials known to the person skilled in the art.

Natural release controlling agents include but are not limited to proteins (e.g., hydrophilic proteins), such as pectin, zein, modified zein, casein, gelatin, gluten, serum albumin, or collagen, chitosan, oligosaccharides and polysaccharides such as cellulose, dextrans, tamarind seed polysaccharide, gellan, carrageenan, xanthan gum, gum Arabic, guar gum, locust bean gum; hyaluronic acid, polyhyaluronic acid, alginic acid, sodium alginate.

Synthetic release controlling agents are selected from but are not limited to polyamides, polycarbonates, polyalkylenes, polyalkylene glycols such as poly(ethylene glycol), polyalkylene oxides, polyalkylene terephthalates, polyvinyl alcohols (PVA), polyvinylphenol, polyvinyl ethers, polyvinyl esters, polyvinyl halides, polyvinylpyrrolidone (PVP), polyglycolides, polysiloxanes, polyurethanes, polystyrene, polylactides, poly(butyric acid), poly(valeric acid), poly (lactide-co-glycolide), poly(ethyleneterephthalate), poly (lactide-co-caprolactone), polyanhydrides (e.g., poly(adipic anhydride)), polyorthoesters, poly(fumaric acid), poly(maleic acid), polyvinyl acetate, polystyrene; polymers of acrylic and methacrylic esters; carbomer, Carbopol®; celluloses and cellulose derivatives such as methyl cellulose (MC), ethyl cellulose (EC), hydroxypropyl cellulose (HPC), hydroxypropylmethyl cellulose (HPMC), hydroxybutylmethyl cellulose, sodium carboxymethyl cellulose, cellulose acetate, cellulose propionate, cellulose acetate butyrate, cellulose acetate phthalate, carboxymethyl cellulose, cellulose triacetate, cellulose sulfate sodium salt and blends and copolymers thereof or mixtures thereof.

A number of pharmaceutical compositions have been developed to release the active ingredients over a defined period of time at a predetermined and controlled rate, which supplies continuously the amount of active ingredient needed to maintain constant serum levels once the steady state is reached. But more often, active ingredient absorption is unsatisfactory and highly variable among and between individuals, despite excellent in vitro release patterns. The reasons for this may be the GI transit of the form, especially its gastric residence time (GRT), which appears to be one of the major causes of the overall transit time variability. Therefore most of the controlled release pharmaceutical compositions fail to achieve its purpose. The active ingredients which are meant for controlled release pharmaceutical composition generally have short half life (less than 4 hours) and need frequent dosing as immediate release pharmaceutical composition. Hence controlled release pharmaceutical compositions of many active ingredients are prepared as once-daily pharmaceutical composition for better patient compliance and better therapeutic effect. But most of the conventional controlled release pharmaceutical compositions have been demonstrated to have suboptimal absorption due to dependence on the transit time of the pharmaceutical composition especially for short half life drugs meant for once daily administration. Shorter transit time of the dosage form in the upper portion of the GIT leading to less exposure time of the active ingredient in a pharmaceutical composition(s) to site of absorption in the GIT. The gastroretentive systems are designed for longer gastric retention of pharmaceutical composition in upper GIT so that there will be more time of exposure of the pharmaceutical composition in the GIT leading to extended period of absorption of the active ingredient.

Generally gastroretentive compositions are desired for those active ingredients which are locally acting or are absorbed locally or are unstable in the alkaline media of lower GI tract. The active ingredients, like tapentadol which are absorbed and has no stability problems through out the GIT, are generally not formulated as gastroretentive pharmaceutical composition. Gastroretentive controlled release composition of tapentadol are not known in the art. We have surprisingly found that the controlled release pharmaceutical composition not only retains the composition in the stomach but it also controls the releases of the active ingredient during the gastroretention and in the later part of the GIT. Thus, there is a controlled release of the active ingredient throughout the sojourn of pharmaceutical composition in the GIT which purposefully achieves the once-daily administration of the pharmaceutical composition thereby increasing patient compliance and thus better therapeutic effect.

In one of the embodiments the above release profile can be achieved by a once daily controlled release pharmaceutical composition comprising controlled release component which is gastroretentive. The controlled release component in an embodiment may be delayed controlled release component or a combination of gastroretentive and delayed controlled release component. The gastroretentive component comprises about 18 to 65% of tapentadol by weight of total weight of tapentadol in the composition and the delayed release component comprises about 32 to 84% of tapentadol by weight of total weight of tapentadol in the composition. The controlled release pharmaceutical composition, which comprises a controlled release gastroretentive component, may further have an immediate release component which allows a rapid onset of action however the controlled release composition may be designed around for rapid onset and prolonged release. The delayed release controlled release component may be osmotic or bioadhesive.

Different techniques that can be used for gastro retention of the pharmaceutical composition includes swelling and expanding systems which are retained by virtue of size of the pharmaceutical composition which is more than the size of the pyloric sphincter e.g. Plug-Type systems. In this type of gastroretentive technique, release controlling agents imbibe water and swell enough to be retained in the upper part of the GIT. The term "swellable" refers to, with respect to a polymer or a polymer matrix or the coating, the polymer or polymer matrix which is capable of imbibing fluid and expanding when in contact with fluid present in the environment of use.

Representative examples of the release controlling agents which swell are selected from, but are not limited to, water-soluble polymers such as polyethylene oxide and cellulosic polymer derivatives including hydroxypropyl cellulose, hydroxypropyl methyl cellulose (HPMC), hydroxyethyl cellulose, sodium carboxy methylcellulose, calcium carboxymethyl cellulose, methyl cellulose, as well as non-cellulosic such as maltodextrin, polyvinyls, polyvinyl alcohol, polyacrylic acids, alginates, gelatin, natural gums, including guar, lightly crosslinked versions of these polymers, starches, starch graft copolymers and the like. The polymers generally have number average molecular weights over 50,000 grams per mole, such as between 50,000 and 10,000,000 grams per mole. Polymers having molecular weights between 300,000 and 8,000 000 grams per mole are preferred, and those having molecular weights between about 2,000,000 to 8,000,000 grams per mole are especially preferred. Polyethylene oxide having a number average molecular weight between about 5,000,000 to 8,000,000 grams per mole is most especially preferred, e.g. Polyox 303 and Polyox 308. Also, especially preferred are methylcellulose type/grade A15C, A4M, A18 M and hydroxypropyl methylcellulose type/grade K4M, K15M, K100M, E4M and F4M (Dow Chemical Company); hydroxyethyl cellulose such as Natrosole HEC; hydroxypropyl cellulose such as Klucel (Grades H, M, G, J, L, E-Aqualon Company); guar such as Supercol® Guar U (Aqualon Company); pectin such as GENU Pectin (Aqualon Company); carrageenan such as GENU Carrageenan (Aqualon Company); poly(methyl vinyl ether/maleic anhydride) such as Gantrez® AN Copolymer (AN-119, -139, -149, -169, -179, GAF Corporation); polyvinyl alcohol such as Elvanol® 71-30, Elvanol® 85-80, Elvanol® 55-65, Elvanol® 50-42 and Elvanol® HV (DuPont); sodium carboxymethyl cellulose such as Aqualon cellulose gum grade 7H4; polyacrylic acids such as Carpobol® resin grades 934P, 940, 941, 971P, 974P, 980, 981, 1382, 2984, 5984, ETD 2001, ETD 2050, calcium polyacrylic acids such as Noveon® resin grades AA-1, CA-1 and CA-2, and sodium polyacrylic acid (BF Goodrich, Cleveland, Ohio). More preferred is hydroxypropyl methylcellulose and combinations thereof.

Another system known as unfoldable systems can also be used in the invention for gastric retention of the composition in which the polymers expand or unfold such that the composition is too large than its original shape to pass from the stomach into the intestine unless enough force is applied to recompress the polymer. They are available in different geometric forms like tetrahedron, ring or planner membrane of polymer.

Another preferred method of gastroretention is to keep the size of the pharmaceutical composition more than the size of the pyloric sphincter. In one of the embodiments at least one dimension of the pharmaceutical composition is 13 mm or more before administration. Other types of gastroretentive techniques used to retain the controlled release pharmaceutical composition in the stomach, are floating systems, raft systems, low-density systems, hydrodynamically balanced systems (HBS), effervescent systems, gas empowered systems, bioadhesive or mucoadhesive systems, high density (sinking) system or non-floating active ingredient delivery system, non-effervescent systems, microballoon/hollow microspheres, super porous hydrogel systems, magnetic systems etc.

In another embodiment, a once daily controlled release pharmaceutical composition of tapentadol, wherein the pharmaceutical composition is a multi-layer composition which may comprise a layer comprising an immediate release component and/or a layer comprising a controlled release component, wherein the controlled release component is gastroretentive or a combination of gastroretentive and delayed controlled release component. The controlled release layer may be bioadhesive or osmotically driven layer or a combination of gastroretentive and bioadhesive or osmotically driven system.

The multi-layered once daily controlled release pharmaceutical composition of the invention can be designed in various methods. One of such multi-layered composition is core-shell type in which the gastroretentive component and delayed controlled release component make a bilayer tablet as a core or a tablet-in-tablet as a core in which delayed controlled release component as inner core and gastroretentive component as outer core and the immediate release component in the form of coating over the core as a shell. Another such multi-layered composition is simple layered type in which gastroretentive component, delayed controlled release and immediate release component form layering by placing one after another to form the composition, in which the immediate release component may be in between the two controlled release i.e. self detachable system or may be present as a top or bottom layer.

The delayed controlled release of active ingredient can be achieved by admixing one or more active ingredients and one or more release controlling agents selected from the group of pH dependent or pH independent polymers, fatty alcohols, fatty acid ester and natural or synthetic waxes etc which will delay the release the active ingredients and one or more pharmaceutically acceptable excipient. Further, delayed controlled release component may be osmotically driven system or bioadhesive.

In yet another embodiment, the once daily controlled release pharmaceutical composition comprising tapentadol is an osmotically driven release system. With an osmotically driven release system, at least one, preferably all, surface(s)

of the release system, preferably those which are in contact or which may come into contact with the release medium, are semi-permeable, preferably provided with a semi-permeable coating, so the surfaces are permeable to the release medium but substantially, and preferably completely, impermeable to the active ingredient, whereby the surface and/or optionally the coating comprises at least one opening for releasing the active ingredient. This is preferably taken to mean a system in tablet form with a delivery opening, an osmotic pharmaceutical composition core, a semi-permeable membrane and a polymeric part which exerts pressure. A useful example of such a system include in particular the OROS® systems such as Push-Pull® system, delayed Push-Pull® system, Multi-Layer Push-Pull® system, the Push-Stick System and in certain cases the L-OROS®. The other types of osmotic active ingredient delivery systems like elementary osmotic pump systems, controlled porosity osmotic pump systems, osmotic bursting osmotic pump systems, monolithic osmotic system, OROS-CT can also be used to achieve a slow release.

In another embodiment, the once daily controlled release pharmaceutical composition comprising tapentadol can be a bioadhesive or mucoadhesive composition, wherein the composition can be retained in any part of the GIT for increasing the GIT residence time, to increase the exposure of the composition to the GIT thus facilitating extended period of absorption of the active ingredient. Bioadhesive and mucoadhesive can be used interchangeably.

The term "pH-dependent polymers" refers to the polymers which are relatively insoluble and impermeable at the pH of the stomach, but which are more soluble or disintegrable or permeable at the pH of the small intestine and colon. The pH-dependent polymers are selected from, but are not limited to, polyacrylamides, phthalate derivatives such as acid phthalates of carbohydrates, amylose acetate phthalate, cellulose acetate phthalate, other cellulose ester phthalates, cellulose ether phthalates, hydroxypropylcellulose phthalate, hydroxypropylethylcellulose phthalate, hydroxypropylmethylcellulose phthalate, methylcellulose phthalate, polyvinyl acetate phthalate, polyvinyl acetate hydrogen phthalate, sodium cellulose acetate phthalate, starch acid phthalate, succinates such as hydroxypropylethylcellulose acetyl succinate, cellulose acetate trimellitate, styrene-maleic acid dibutyl phthalate copolymer, styrene-maleic acid polyvinylacetate phthalate copolymer, styrene and maleic acid copolymers, polyacrylic add derivatives such as acrylic acid and acrylic ester copolymers, polymethacrylic acid and esters thereof, poly acrylic methacrylic add copolymers, shellac, and vinyl acetate and crotonic add copolymers and combinations thereof.

Preferred pH-dependent polymers include shellac, phthalate derivatives, particularly cellulose acetate phthalate, polyvinylacetate phthalate, and hydroxypropylmethylcellulose phthalate; cellulose acetate trimellitate; polyacrylic acid derivatives, particularly copolymers comprising acrylic acid and at least one acrylic acid ester, polymethyl methacrylate blended with acrylic add and acrylic ester copolymers; and vinyl acetate and crotonic acid copolymers.

A particularly preferred group of pH-dependent polymers includes cellulose acetate phthalate, polyvinylacetate phthalate, hydroxypropylmethylcellulose phthalate, anionic acrylic copolymers of methacrylic acid and methylmethacrylate, and copolymers comprising acrylic acid and at least one acrylic add ester. More preferred delayed release polymer is anionic acrylic copolymers of methacrylic acid and methylmethacrylate. Copolymers of this type are available from RöhmPharma Corp, under the trademarks Eudragit®-L and Eudragit®-S. Eudragit®-L and Eudragit®-S are anionic copolymers of methacrylic add and methylmethacrylate. Mixtures of Eudragit®-L and Eudragit®-S may also be used.

The pH-independent polymers for delayed controlled release of active ingredients are the release controlling agents which delay the release of the active ingredients from the composition. Non limiting examples of this type of polymers include cellulosic derivatives including ethylcellulose, hydroxypropyl cellulose, hydroxypropyl methyl cellulose, hydroxyethyl cellulose, sodium carboxy methylcellulose, calcium carboxymethyl cellulose, methyl cellulose, as well as noncellulosics such as maltodextrin, polyvinyls, polyvinyl alcohol, and co-polymers of acrylic and methacrylic acid esters (Eudragit® RS or RL).

Various natural or synthetic waxes may be used. These waxes can originate from animal, vegetable, or mineral sources. Preferably, the wax used may be synthetic in origin. Most preferably, the wax is a long chain polymer of ethylene with a molecular weight between about 500 and about 2000. Such compounds are referred to herein as polyethylene waxes. Other synthetic waxes such as carbowaxes and halowaxes can also be used.

Delaying release of active ingredient can also be achieved by coating the powder, granules, pellets, tablets, minitablets, capsules of the active ingredients or a mixture of active ingredient and excipients with the release delaying agents. Delaying release of active ingredient can also be achieved by coating inert core with a matrix of active ingredients and the release delaying agents. The active ingredients and release delaying agents are dissolved or dispersed in a suitable solvent and then coated the inert core by different techniques known in art.

Non limiting examples of binders include starches such as potato starch, wheat starch, corn starch, celluloses such as hydroxypropyl cellulose (HPC), hydroxyethyl cellulose, hydroxypropylmethyl cellulose (HPMC), ethyl cellulose, sodium carboxy methyl cellulose; natural gums like acacia, alginic acid, guar gum; liquid glucose, dextrin, povidone, syrup, polyethylene oxide, polyvinyl pyrrolidone, poly-N-vinyl amide, polyethylene glycol, gelatin, poly propylene glycol, tragacanth, combinations there of and other materials known to one of ordinary skill in the art and mixtures thereof.

Fillers or diluents include, but are not limited to dextrates, dextrin, dextrose, fructose, lactitol, mannitol, sucrose, starch, lactose, xylitol, sorbitol, talc, microcrystalline cellulose, calcium carbonate, calcium phosphate dibasic or tribasic, calcium sulphate or mixtures thereof.

Lubricants may be selected from, but are not limited to, those conventionally known in the art such as magnesium, aluminium or calcium or zinc stearate, polyethylene glycol, glyceryl behenate, mineral oil, sodium stearyl fumarate, stearic acid, hydrogenated vegetable oil and talc or mixtures thereof.

Glidants include, but are not limited to, silicon dioxide, magnesium trisilicate, powdered cellulose, starch, talc and tribasic calcium phosphate, calcium silicate, magnesium silicate, colloidal silicon dioxide, silicon hydrogel or mixtures thereof.

The controlled release pharmaceutical composition(s) may optionally contain a surface-active agent or solubilizing agents. Solubilizing agents help to solubilize the active ingredient either in composition or in-situ at the site of absorption or action. Solubilizing agents include but are not limited to surfactants, cyclodextrin and its derivatives, lipophilic substances or any combination thereof. Non-limiting examples of surfactants include water soluble or water dispersible nonionic, semi-polar nonionic, anionic, cationic, amphoteric, or zwitterionic surface active agents or any combination thereof.

The preferred surface active agents include, but are not limited to, copolymers composed of a central hydrophobic chain of polyoxypropylene (poly(propylene oxide)) and polyoxyethylene (poly(ethylene oxide)) that is well known as poloxamer. However, other agents may also be employed such as dioctyl sodium sulfosuccinate (DSS), triethanolamine, sodium lauryl sulphate (SLS), polyoxyethylene sorbitan and poloxalkol derivatives, quaternary ammonium salts or other pharmaceutically acceptable surface active agents known to the person skilled in the art. Other solubilizing agents include but not necessarily limited to vitamin E and its derivatives; monohydric alcohol esters such as trialkyl citrates, lactones and lower alcohol fatty acid esters; nitrogen-containing solvents; phospholipids; glycerol acetates such as acetin, diacetin and triacetin; glycerol fatty acid esters such as mono-, di- and triglycerides and acetylated mono- and di-glycerides; propylene glycol esters; ethylene glycol esters and combinations thereof.

The controlled release pharmaceutical composition(s) may optionally contain one or more osmogen such as salts, acids, bases, chelating agents in the composition. The active ingredient itself may act as an osmogen. Typical classes of suitable osmogens are water-soluble organic acids, salts and sugars that are capable of imbibing water to thereby affect an osmotic pressure gradient across the barrier of the surrounding coating. Typical useful osmogens include magnesium sulfate, magnesium chloride, calcium chloride, sodium chloride, lithium chloride, potassium sulfate, sodium carbonate, sodium sulfite, lithium sulfate, potassium chloride, sodium sulfate, mannitol, xylitol, urea, sorbitol, inositol, raffinose, sucrose, glucose, fructose, lactose, citric acid, succinic acid, tartaric acid calcium bicarbonate, calcium sulfate, calcium lactate, alpha-d-lactose monohydrate, and the other similar or equivalent materials and combination thereof. Particularly preferred osmogens are glucose, lactose, sucrose, mannitol, xylitol and sodium chloride.

The amount of each type of excipient employed, e.g. osmogen, glidant, binder, disintegrant, filler or diluent and lubricant may vary within ranges conventional in the art. Thus for example, the amount of osmogen may vary within a range of 5-40% by weight, in particular 10 to 30% by weight, e.g. 15 to 30% by weight; the amount of glidant may vary within a range of 0.1 to 10% by weight, in particular 0.1 to 5% by weight, e.g. 0.1 to 0.5% by weight; the amount of binder may vary within a range of from about 10 to 45% by weight, e.g. 20 to 30% by weight; the amount of disintegrant may vary within a range of from 0.5 to 5% by weight, e.g. 1% by weight; the amount of filler or diluent may vary within a range of from 10 to 60% by weight; whereas the amount of lubricant may vary within a range of from 0.1 to 5.0% by weight.

The once daily controlled release pharmaceutical composition may be manufactured by various methods such as by dry granulation, wet granulation, melt granulation, direct compression, double compression, extrusion spheronization and layering. The process may be carried out under ambient conditions of temperature and humidity.

The once daily controlled release pharmaceutical composition may optionally have one or more non-functional coatings such as film coating or sugar coating, which has no or negligible impact on release of active ingredient form the composition. The controlled release pharmaceutical composition may further have one or more functional coating such as bioadhesive coating, diffusion coatings, non-permeable coating and semi-permeable coating, which modify the release of active ingredients from the composition.

The coating layers may comprise one or more excipients selected from the group comprising coating agents, opacifiers, taste-masking agents, fillers, polishing agents, colouring agents, antitacking agents, pore forming agents and the like.

Coating agents include, but are not limited to, polysaccharides such as maltodextrin, alkyl celluloses such as methyl or ethyl cellulose, hydroxyalkylcelluloses (e.g. hydroxypropylcellulose or hydroxypropylmethylcelluloses); polyvinylpyrrolidone, acacia, corn, sucrose, gelatin, shellac, cellulose acetate pthalate, lipids, synthetic resins, acrylic polymers, opadry, polyvinyl alcohol (PVA), copolymers of vinylpyrrolidone and vinyl acetate (e.g. marketed under the brand name of Plasdone®) and polymers based on methacrylic acid such as those marketed under the brand name of Eudragit®.

The coating may be applied from aqueous or non-aqueous systems or combinations of aqueous and non-aqueous systems as appropriate. Excipients can be included along with the film formers to obtain satisfactory films. These excipients can include plasticizers such as dibutyl phthalate, triethyl citrate, polyethylene glycol (PEG) and the like, antitacking agents such as talc, stearic acid, magnesium stearate and colloidal silicon dioxide and the like, surfactants such as polysorbates and sodium lauryl sulphate, fillers such as talc, precipitated calcium carbonate, polishing agents such as beeswax, carnauba wax, synthetic chlorinated wax and opacifying agents such as titanium dioxide and the like. All these excipients can be used at levels well known to the persons skilled in the art. The coating can be done by any method known in the art. Various coating methods known in the art are pan coating, spray coating, compression coating, dip coating etc.

Combinations of various analgesics have also been prepared to avoid the side effects associated with these active ingredients, and the combinations are noted to have the benefit of requiring less of each ingredient and may provide additive effects. One of the embodiments relates to once daily controlled release pharmaceutical composition comprising tapentadol and/or one or more other active ingredient. The composition may comprise immediate release component and/or a controlled release component. The controlled release component may be gastroretentive or bioadhesive or osmotic or a delayed controlled release component or combinations thereof. The immediate release component may comprise tapentadol and/or one or more active ingredient such as meloxicam or combinations thereof. Tapentadol may be combined or administered simultaneously with one or more active ingredients such as analgesics; anesthetics; antiarthritic agents; respiratory drugs; anticancer agents; anticholinergics; anticonvulsants; antidepressants; antidiabetics; antidiarrheals; antihelminthics; antihistamines; antihyperlipidemics; antihypertensives, antianginal agents; vasodilators; anti-infectives such as antibiotics and antivirals; antiinflammatories; antimigraine agents; antinauseants; antineoplastics; anti-Parkinson agents; antipruritics; antipsychotics; antipyretics; antispasmodics; antitubercular agents; antiulcer agents and other gastrointestinally active agents; anxiolytics; appetite suppressants; attention deficit disorder (ADD) and attention deficit hyperactivity disorder (ADHD) drugs; CNS agents & vasodilator agents; beta-blockers and antiarrhythmic agents; antiallergic, decongestants; diuretics; herbal remedies; hormonolytics; hypnotics; hypoglycemic agents; immunosuppressive agents; leukotriene inhibitors; mitotic inhibitors; muscle relaxants; narcotic antagonists; nutritional agents, such as vitamins, essential amino acids and fatty acids; parasympatholytics; psychostimulants; sedatives; steroids; sympathomimetics; and tranquilzer and combinations thereof, preferably with other analgesics such as Acetylsalicylic Acid, Apazone, Paracetamol, Codeine, Dihydrocodeine, Dexibuprofen, Alminoprofen, Carbasalate, Desflurane, Diflunisal, Enflurane, Etodolac, Etomidate, Floctafenine, Fosfosal, Isoflurane, Isonixin, Ketorolac, Lornoxicam, Clonixinate, Midazolam, Mofezolac, Naproxen, Nefopam, Propofol, Rimazolium, Rofecoxib, Ropivacaine, Sevoflurane, Parecoxib, Zaltoprofen, Acemetacin, Sulindac, Indomethacin, Mefenamic Acid, Ketoprofen, Diclofenac, Piroxicam, Flupirtine, Mofezolac, Ibuprofen, Fenoprofen, Flurbiprofen, Amtolmentin, Fepradinol, Celecoxib, Valdecoxib, Etoricoxib, Fluproquazon, Nefopam, Asthaxantin, or other analgesics known in art and mixtures thereof, preferably meloxicam. The maximum recommended daily oral dose of meloxicam is 15 mg. The pharmaceutical composition of combination of meloxicam and tapentadol comprises meloxicam from 5 to 15 mg and tapentadol from 50 to 700 mg. The various preferable doses of combinations of tapentadol/meloxicam are 100/7.5 mg, 100/7.5 mg, 150/7.5 mg, 150/15 mg, 200/7.5 mg, 200/15 mg, 300/7.5 mg, 300/15 mg, 400/7.5 mg and 400/15 mg. The other preferable combination pharmaceutical composition includes diclofenac or indomethacin. The diclofenac is present in the pharmaceutical composition ranges from of 10 mg to 200 mg, preferably 25 mg to 150 mg. The indomethacin present in the pharmaceutical composition ranges from 10 mg to 100 mg, preferably 25 mg to 75 mg. These active ingredients may exist as either solids or liquids at standard temperature and pressure.

In another embodiment the once daily controlled release pharmaceutical comprising tapentadol or combinations with other active ingredients can be used for the treatment of pain. The pain can be acute or chronic and may vary from mild to moderate to severe. Treatment of pain includes but not limited to treatment of, chronic low back pain, acute low back pain, acute pain after abdominal hysterectomy, acute pain from bunionectomy, postoperative pain following bunionectomy surgery, acute pain after hip replacement surgery, moderate to severe chronic pain due to osteoarthritis of the knee chronic tumor related pain, chronic malignant tumor related pain, cancer pain, chronic malignant tumor-related cancer pain, awaiting joint replacement surgery, post-surgical pain in children and adolescents, acute pain from vertebral compression fracture associated with osteoporosis, treatment of acute post-operative pain following elective arthroscopic shoulder surgery, treatment of moderate to severe pain in subjects with knee osteoarthritis, treatment in patients with end-stage joint disease, painful diabetic peripheral neuropathy, moderate to severe pain due to chronic, painful diabetic peripheral neuropathy (DPN), treatment of chronic tumor related pain, postherpetic neuralgia. The once daily controlled release pharmaceutical comprising tapentadol or combinations with other active ingredients can also be used for treatment of other diseases known in art.

The following experimental details are set forth to aid in an understanding of the invention, and are not intended, and should not be construed, to limit in any way the invention set forth in the claims that follow thereafter.

EXAMPLES 1-8

| Ingredients | % w/w of ingredients in the following examples | | | | | | | |
|---|---|---|---|---|---|---|---|---|
| | 1 | 2 | 3 | 4 | 5 | 6 | 7 | 8 |
| Controlled Release component | | | | | | | | |
| Tapentadol HCl eq to Tapentadol | 12.0 | 12.0 | 10.5 | 10.5 | 12.0 | 12.0 | 10.5 | 10.5 |
| Hydroxy propyl methyl cellulose | 18.0 | 18.0 | 20.0 | 20.0 | 18.0 | 18.0 | 20.0 | 20.0 |
| Lactose Monohydrate | 2.0 | 2.0 | 2.0 | 2.0 | 2.0 | 2.0 | 2.0 | 2.0 |
| Microcrystalline cellulose | 2.0 | 2.0 | 2.0 | 2.0 | 2.0 | 2.0 | 2.0 | 2.0 |
| Silicon dioxide | 0.3 | 0.3 | 0.2 | 0.2 | 0.3 | 0.3 | 0.2 | 0.2 |
| Magnesium stearate | 0.2 | 0.2 | 0.2 | 0.2 | 0.2 | 0.2 | 0.2 | 0.2 |
| Delayed Controlled Release component | | | | | | | | |
| Tapentadol HCl eq to Tapentadol | 17.0 | 17.0 | 18.0 | 18.0 | 17.0 | 17.0 | 18.0 | 18.0 |
| Eudragit | 6.0 | 6.0 | 6.0 | 6.5 | 6.0 | 6.0 | 6.0 | 6.5 |
| Hydroxy propyl methyl cellulose | 21.0 | 21.0 | 20.0 | 20.0 | 20.0 | 21.0 | 20.0 | 20.0 |
| Microcrystalline cellulose | 4.0 | 4.0 | 4.0 | 4.0 | 4.0 | 4.0 | 4.0 | 4.0 |
| Lactose Monohydrate | 5.0 | 5.0 | 5.0 | 5.0 | 5.0 | 5.0 | 5.0 | 5.0 |
| Magnesium stearate | 0.3 | 0.3 | 0.2 | 0.3 | 0.3 | 0.3 | 0.3 | 0.3 |
| Silicon dioxide | — | — | 0.3 | — | — | — | 0.2 | — |
| Immediate Release Component | | | | | | | | |
| Tapentadol HCl eq to Tapentadol | 3.0 | 3.0 | 3.5 | 3.5 | 3.0 | 3.0 | 3.5 | 3.5 |
| Meloxicam | | | | | 1.5 | 1.5 | 1.5 | 1.5 |
| Polyvinyl pyrrolidone | 3.4 | 3.4 | 0.5 | 0.5 | 3.0 | 1.9 | 0.5 | 0.5 |
| Hydroxy propyl methyl cellulose | 3.5 | 3.5 | — | — | 3.2 | 3.5 | — | — |
| Polyethylene glycol | 2.0 | 2.0 | | | 2.0 | 2.0 | | |
| Lactose Monohydrate | — | — | 3.5 | 3.5 | | | 3.0 | 2.0 |
| Microcrystalline cellulose | — | — | 3.5 | 3.1 | | | 2.5 | 3.1 |

-continued

| Ingredients | % w/w of ingredients in the following examples | | | | | | | |
|---|---|---|---|---|---|---|---|---|
| | 1 | 2 | 3 | 4 | 5 | 6 | 7 | 8 |
| Croscarmellose Sodium | — | — | 0.5 | 0.5 | — | — | 0.5 | 0.5 |
| Magnesium stearate | — | — | 0.1 | 0.2 | | | 0.1 | 0.2 |
| Silicon Dioxide | 0.3 | 0.3 | | — | 0.5 | 0.3 | — | — |

Manufacturing Procedure of Example 1:
A) Controlled release component (Layer): Tapentadol HCl, hydroxyl propyl methyl cellulose, lactose monohydrate, and microcrystalline cellulose were sifted through a suitable sieve and mixed well. Sifted silicon dioxide and magnesium stearate were mixed well with the tapentadol mixture.
B) Delayed Controlled Release Component (Layer): Tapentadol HCl, Eudragit, hydroxyl propyl methyl cellulose, lactose monohydrate, and microcrystalline cellulose were sifted through a suitable sieve, mixed well and then lubricated with sifted magnesium stearate.
C) Immediate release component (Coating): Polyvinyl pyrrolidone K30 was added in sufficient quantity of water followed by hydroxy propyl methyl cellulose, polyethylene glycol, with continuous stirring to prepare a slurry and then Tapentadol HCl and silicon dioxide was added in the slurry to prepare a dispersion.
D) The delayed controlled release component was compressed with suitable hardness followed by the blend of controlled release component into a bilayer tablet using 13.3 mm round shape punch with suitable parameters.
E) The compressed tablet was coated with the immediate release component dispersion.

Manufacturing Procedure of Example 2:
A) The controlled release component (Outer core), delayed controlled Release Component (Inner core) and immediate release component (Outer shell) were prepared like example 1.
B) The delayed controlled release component blend was compressed with suitable punch with suitable hardness. The controlled release component blend was compressed using the delayed controlled release component tablet as inner core to prepare a tablet in tablet type composition. The final compressed tablet of both the components was further coated with dispersion of immediate release component.

Manufacturing Procedure of Example 3:
A) The controlled release component (layer) and delayed controlled Release Component (layer) were prepared like example 1.
B) Immediate Release Component (Layer): Tapentadol HCl, lactose monohydrate, part of microcrystalline cellulose & croscarmellose sodium were sifted through a suitable sieve, mixed well and granulated with a solution of polyvinyl pyrrolidone dissolved in sufficient quantity of water. The granules were dried till its moisture content of the granules remained not more than 1.5% w/w, sized by using a suitable sieve and mixed with sifted remaining of the croscarmellose sodium and magnesium stearate.
C) The delayed controlled release component blend was compressed followed by controlled release component blend and finally granules of immediate release component using 13.3 mm round shape punch with suitable parameters to prepare a triple layered tablet in which controlled release component was present in between immediate release component and delayed controlled release component.

Manufacturing Procedure of Example 4:
The process was same as example 3 except immediate release component was present in between the controlled release component and the delayed controlled release component i.e. compression was started with delayed controlled component followed by immediate release component and finally controlled release component over the immediate release component.

Manufacturing Procedure of Example 5:
The composition of example 5 was prepared like example 1 except meloxicam was added to the dispersion of immediate release component along with tapentadol and silicon dioxide.

Manufacturing Procedure of Example 6:
The composition of example 6 was prepared like example 2 except meloxicam was added to the dispersion of immediate release component along with tapentadol and silicon dioxide.

Manufacturing Procedure of Example 7:
The composition of example 7 was prepared like example 3 except meloxicam was added to immediate release component along with tapentadol.

Manufacturing Procedure of Example 8:
The composition of example 8 was prepared like example 4 except meloxicam was added to immediate release component along with tapentadol.

The delayed controlled release component can also be prepared by various methods such as—
(a) By hot melt extrusion technique using enteric polymers

| Ingredients | % w/w* |
|---|---|
| Tapentadol HCl eq to Tapentadol | 18.0 |
| Eudragit | 6.5 |
| Hydroxy propyl methyl cellulose acetate succinate (HPMCAS) | 20.0 |
| Triethyl citrate | 4.0 |
| Hydroxy propyl methyl cellulose | 5.0 |
| Magnesium Stearate | 0.3 |

*% w/w of the total composition

Manufacturing procedure: Tapentadol HCl, Eudragit, hydroxyl propyl methyl celluloses were mixed in suitable proportion followed by triethyl citrate and passed through hot melt extruder with extrudes sized through suitable mesh sieve. The extrudes were mixed well with HPMCAS, dried and finally lubricated with magnesium stearate.

(b) By coating the Tapentadol HCl pellets with enteric coating polymers

| Ingredients | % w/w* |
|---|---|
| Tapentadol HCl eq to Tapentadol | 18.0 |
| Microcrystalline cellulose | 4.0 |
| Lactose Monohydrate | 4.0 |
| Eudragit | 10.0 |
| Hydroxy propyl methyl cellulose acetate succinate (HPMCAS) | 8.0 |
| Hydroxy propyl methyl cellulose | 7.5 |
| Triethyl citrate | 1.8 |
| Isopropyl alcohol | q.s. |
| Dichloro methane-Methanol Mixture (40:60) | q.s. |
| Magnesium Stearate | 0.5 |

*% w/w of the total composition

Manufacturing procedure: Tapentadol HCl, lactose monohydrate, microcrystalline cellulose, eudragit and hydroxyl propyl methyl cellulose were mixed well and granulated with suitable quantity of water. The granulated wet mass was passed through an extruder through suitable screen and then spheronized with a spheronizer with optimum speed & time. The spheronized pellets were dried and coated with a solution of HPMCAS in isopropyl alcohol, dichloro-methane-methanol mixture along with triethyl citrate, using fluid bed processor with suitable parameters. Finally the coated pellets were lubricated using magnesium Stearate.

(c) By coating the Tapentadol HCl on carrier with enteric coating polymers

| Ingredients | % w/w* |
|---|---|
| Tapentadol HCl eq to Tapentadol | 18.0 |
| Non pareil beads | 12.0 |
| Eudragit | 8.0 |
| Hydroxy propyl methyl cellulose acetate succinate (HPMCAS) | 8.0 |
| Ethyl Cellulose | 5.5 |
| Triethyl citrate | 1.8 |
| Isopropyl alcohol | q.s. |
| Dichloro methane-Methanol Mixture (40:60) | q.s. |
| Magnesium Stearate | 0.5 |

*% w/w of the total composition

Manufacturing procedure: Eudragit, HPMCAS, ethyl cellulose were dissolved in isopropyl alcohol, dichloro methane-methanol mix (40:60) along with triethyl citrate. Tapentadol HCl was added to the above solution and then the drug solution was loaded over non-pareil beads by spry drying method in fluidized bed processor using suitable parameters to prepare drug loaded pellets. The drug loaded pellets were further lubricated with magnesium stearate.

EXAMPLE 9

| Ingredients | % w/w |
|---|---|
| Hydrophobic polymer granules | |
| Tapentadol HCl eq to tapentadol | 8.5 |
| Sterotex | 8.5 |
| Ethyl Cellulose | 4.5 |
| Polyethylene glycol | 2.0 |
| Stearic acid | 1.0 |
| Hydrophilic polymer granules | |
| Tapentadol HCl eq to tapentadol | 17.5 |
| Hydroxy propyl methyl cellulose | 20.0 |
| Xanthan Gum | 15.0 |
| Lactose | 7.0 |
| Povidone | 1.5 |
| Extra-granular composition | |
| Lactose monohydrate | 13.0 |
| Colloidal silicon dioxide | 1.0 |
| Magnesium Stearate | 0.5 |

Manufacturing Procedure:

A) Hydrophobic Polymer Granules: All ingredients were sifted through suitable sieve. Sterotex and polyethylene glycol were melted in preheated steam jacketed vessel at 60-70° C. and to this melted mass Tapentadol HCl and stearic acid were added under stirring. Then heating was stopped but stirring was continued for 30-45 min until a uniform mass is formed. The molten uniform mass was cooled to room temperature, milled the solidified mass in co-mill using suitable sieve and finally sifted dried granules through suitable sieve. The granules were mixed with lactose monohydrate and silicon dioxide and then lubricated with magnesium stearate.

B) Hydrophilic Polymer Granules: Tapentadol HCl, lactose, hydroxy propyl methyl cellulose and xanthan gum were sifted, mixed well and granulated with povidone. The granules were dried and sized through suitable sieve. The granules were mixed with lactose monohydrate and silicon dioxide and then lubricated with magnesium stearate.

C) The hydrophobic and hydrophilic polymer granules were compressed into bilayered tablets using suitable shaped punches and dies (13.3 mm round punch/21.1×9.7 oval shape punch).

EXAMPLE 10

| Ingredients | % w/w |
|---|---|
| Controlled Release layer | |
| Tapentadol HCl eq to tapentadol | 30.0 |
| Polyvinyl pyrrolidone | 2.5 |
| Hydroxy propyl methyl cellulose | 40.0 |
| Lactose Monohydrate | 5.5 |
| Eudragit | 5.0 |
| Micro crystalline cellulose | 5.0 |
| Magnesium stearate | 0.5 |
| Purified water and isopropyl alcohol mixture | q.s. |
| Inert layer | |
| Sterotex | 8.5 |
| Eudragit | 2.0 |
| Silicon dioxide | 0.5 |
| Magnesium stearate | 0.5 |

Manufacturing procedure: Tapentadol HCl, a part of sterotex, hydroxy propyl methyl cellulose, a part of Eudragit, lactose and microcrystalline cellulose were mixed well and granulated using polyvinyl pyrrolidone solution in water and isopropyl alcohol mixture. The granules were dried, sifted and lubricated with magnesium stearate. Remaining part of sterotex and Eudragit were mixed, lubricated and compressed with granules of tapentadol into bilayered tablets using suitable shaped punches and dies (13.3 mm round punch/21.1×9.7 oval shape punch).

EXAMPLE 11

| Ingredients | % w/w |
| --- | --- |
| Tapentadol HCl eq to Tapentadol | 60.0 |
| Polyvinyl pyrrolidone | 3.0 |
| Mannitol | 15.0 |
| Lactose monohydrate | 5.0 |
| Microcrystalline cellulose | 4.5 |
| Magnesium stearate | 0.5 |
| Purified water | q.s. |
| Cellulose acetate | 9.0 |
| Polyethylene glycol (PEG) | 2.0 |
| Triacetine | 1.0 |
| Acetone | q.s. |

Manufacturing procedure: Tapentadol HCl, mannitol, and lactose monohydrate were sifted through suitable sieve (40 #SS), mixed well and granulated with an aqueous solution of polyvinyl pyrrolidone as binder. The granules were dried, sized, lubricated with magnesium stearate and compressed using round shaped punches of suitable size. The compressed tablets were coated with a solution of cellulose acetate, triacetin and polyethylene glycol in acetone. Laser drilling technology was be used to drill orifice/pore on one/both side.

EXAMPLE 12

| Ingredients | % w/w |
| --- | --- |
| Core | |
| Active layer | |
| Tapentadol HCl eq to Tapentadol | 25.0 |
| Polyvinyl pyrrolidone | 33.0 |
| Mannitol | 15.0 |
| Polyethylene oxide | 10.0 |
| Magnesium stearate | 0.5 |
| Isopropyl alcohol | q.s. |
| Push-pull layer | |
| Polyethylene oxide | 10.0 |
| Potassium chloride | 15.0 |
| Hypromellose | 5.0 |
| Hydroxy propyl cellulose | 2.0 |
| Magnesium stearate | 0.5 |
| Coating (5-15% wt. gain) | |
| Cellulose acetate | 9.0 |
| Polyethylene glycol | 4.0 |
| Triacetin | 1.0 |
| Acetone | q.s. |

Manufacturing Procedure:
A) Active layer: Tapentadol HCl, mannitol and Polyethylene oxide were sifted, mixed well and granulated with binder solution (povidone in isopropyl alcohol). The granules were dried, sized and lubricated with magnesium stearate.
B) Push-pull layer: Polyethylene oxide, potassium chloride, hypromellose and hydroxy propyl cellulose were sifted, mixed well and lubricated with magnesium stearate.
C) The active layer and push-pull layer were compressed into a bilayered tablet using suitable size and shape punch; and coated with a solution of cellulose acetate, triacetine and polyethylene glycol in acetone. Laser drilling technology was used to drill orifice/pore on one/both.

EXAMPLE 13

| Ingredients | % w/w* |
| --- | --- |
| Tapentadol HCl eq to Tapentadol | 30.0 |
| Polyvinyl pyrrolidone | 4.0 |
| Hydroxy propyl methyl cellulose | 15.0 |
| Sterotex | 15.0 |
| Lactose monohydrate | 15.0 |
| Microcrystalline cellulose | 20.0 |
| Magnesium stearate | 1.0 |
| Purified water | q.s. |
| Opadry coat (non-functional) | For 2-5% wt. gain |

*As percentage of the core tablet weight

Manufacturing procedure: Tapentadol HCl, microcrystalline cellulose and lactose monohydrate were sifted through suitable sieve (40 #SS), mixed well and granulated with aqueous solution of polyvinyl pyrrolidone as binder. The granules were dried, sized and mixed with hydroxy propyl methyl cellulose and sterotex either alone or in combination. The above blend was lubricated with magnesium stearate and compressed using suitable size & shape punch. The compressed tablets were further coated using opadry coating dispersion.

EXAMPLE 14

| Ingredients | % w/w |
| --- | --- |
| Tapentadol HCl eq to tapentadol | 35.0 |
| Polyvinyl pyrrolidone | 4.0 |
| Lactose monohydrate | 25.0 |
| Microcrystalline cellulose | 20.0 |
| Magnesium stearate | 1.0 |
| Purified water | q.s. |
| Ethyl cellulose | 10.0 |
| Polyethylene glycol (PEG) | 5.0 |
| Isopropyl alcohol, dichloromethane and acetone mixture | q.s. |

Manufacturing procedure: Tapentadol HCl, microcrystalline cellulose and lactose monohydrate were sifted through sieve (40 #SS), mixed well and granulated using aqueous solution of polyvinyl pyrrolidone as binder. The granules were dried, sized, lubricated with magnesium stearate and compressed using suitable size & shape punch. The compressed tablets were coated using solution of ethyl cellulose with or without polyethylene glycol in isopropyl alcohol, dichloromethane and acetone mixture.

EXAMPLE 15

| Ingredients | % w/w* |
| --- | --- |
| Tapentadol HCl eq to tapentadol | 30.0 |
| Sterotex | 37.0 |
| Microcrystalline cellulose | 15.0 |
| Stearic acid | 5.0 |
| Polyethylene glycol | 10.0 |
| Colloidal silicon dioxide | 2.0 |
| Magnesium stearate | 1.0 |
| Opadry | For 2-3% wt gain |

*As percentage of the core tablet weight

Manufacturing procedure: All ingredients were sifted through suitable sieve. Sterotex and polyethylene glycol were melted in preheated steam jacketed vessel at 60-70° C.

and Tapentadol HCl and stearic acid were added to the melted mass under stirring. Heating was stopped after proper mixing but stirring continued for 30-45 min until a uniform mass was formed. The molten uniform mass was cooled to room temperature and the solidified mass was milled in co-mill using suitable sieve to prepare granules. The above granules were mixed with microcrystalline cellulose, followed by colloidal silicon dioxide and magnesium stearate and then compressed into tablet using suitable punch tooling. The compressed tablets were further coated with Opadry solution.

EXAMPLE 16

| Ingredients | % w/w |
|---|---|
| Tapentadol HCl eq to tapentadol | 40.0 |
| Hydroxy propyl methyl cellulose | 20.0 |
| Ethyl cellulose | 5.0 |
| Water and alcohol mixture | q.s. |
| Microcrystalline cellulose spheres | 35.0 |

Manufacturing procedure: All ingredients were sifted through suitable sieve. Tapentadol HCl, hydroxy propyl methyl cellulose and ethyl cellulose in water and alcohol mixture under stirring and loaded on microcrystalline cellulose spheres using spray dry method in fluidized bed processor form pellets. The drug-loaded pellets were filled in the capsules.

EXAMPLE 17

| Ingredients | mg/Tab |
|---|---|
| Tapentadol HCl | 349.5 |
| Lactose monohydrate | 125 |
| Hdrogenated vegetable oil (Sterotex) | 650 |
| PEG 6000 | 13.5 |
| Hydroxy propyl methyl cellulose (K100 LVCR) | 50 |
| Microcrystalline cellulose | 33 |
| Colloidal silicon dioxide | 3 |
| Magnesium stearate | 1 |
| Opadry coat | For 2-5% wt. gain |

*As percentage of the core tablet weight

Manufacturing procedure: All ingredients were sifted through suitable sieve. Sterotex and polyethylene glycol were melted in preheated steam jacketed vessel at 60-70° C. and Tapentadol HCl was added to the melted mass under stirring. Heating was stopped after a tapentadol was mixed well but stirring continued for 30-45 min until a uniform mass was formed. The molten uniform mass was cooled to room temperature and the solidified mass was milled in co-mill using suitable sieve to prepare granules. The above granules were mixed with microcrystalline cellulose, followed by colloidal silicon dioxide and magnesium stearate; and compressed into tablet using suitable punch tooling. The compressed tablets were further coated with Opadry solution.

EXAMPLE 18-21

| Ingredients | Example 18 | Example 19 | Example 20 | Example 21 |
|---|---|---|---|---|
| % w/w of ingredients in the following examples | | | | |
| Immediate Release component | | | | |
| Tapentadol HCl | 3.3 | 3.1 | 1.9 | 1.9 |
| Lactose Monohydrate | 3.4 | 3.2 | 3.2 | 3.1 |
| Microcrystalline Cellulose | 3.5 | 3.4 | 3.4 | 3.2 |
| Crosscarmellose Sodium | 0.3 | 0.3 | 0.3 | 0.3 |
| Polyvinyl pyrrolidone (PVP) | 0.4 | 0.4 | 0.4 | 0.4 |
| Magnesium Stearate | 0.1 | 0.1 | 0.1 | 0.1 |
| Controlled Release component | | | | |
| Tapentadol HCl | 11.1 | 10.5 | 7.6 | 16.4 |
| Polyvinyl pyrrolidone | 0 | 0.9 | 0.9 | 0 |
| Hydrogenated Vegetable Oil | 0 | 0 | 0 | 27 |
| Lactose Monohydrate | 2.5 | 2.1 | 3.2 | 5.5 |
| Microcrystalline Cellulose | 2.3 | 1.8 | 1.8 | 1.8 |
| PEG 6000 | 0 | 0 | 0 | 1.3 |
| HPMC K100M Premium CR | 23 | 21.8 | 16 | 3.5 |
| HPMC K100 LVCR | 0 | 0 | 2.3 | 0 |
| Aerosil 200 | 0.2 | 0.2 | 0.2 | 0.2 |
| Magnesium Stearate | 0.1 | 0.1 | 0.1 | 0.1 |
| Delayed Controlled Release component | | | | |
| Tapentadol HCl | 18.8 | 18 | 22 | 12 |
| Polyvinyl pyrrolidone (PVP) | 0 | 1.3 | 1.4 | 1.3 |
| Microcrystalline Cellulose | 4.8 | 4 | 4 | 2.9 |
| Lactose Monohydrate | 5.1 | 4.5 | 7.8 | 4 |
| Eudragit L 100 | 5.7 | 5.4 | 7.3 | 4.8 |
| HPMC K100M Premium CR | 7.1 | 11.1 | 11.4 | 7.4 |
| HPMC K100 LVCR | 8.1 | 7.6 | 4.5 | 2.6 |
| Magnesium Stearate | 0.2 | 0.2 | 0.2 | 0.2 |

Manufacturing Procedure of Example 18:
A) Immediate Release Component: Tapentadol HCl, lactose monohydrate, a part of microcrystalline cellulose and croscarmellose sodium were sifted through sieve (40 #SS), mix well and granulated with a solution of PVP in sufficient quantity of water. The granules were dried, sized and mixed remaining part of microcrystalline cellulose and croscarmellose sodium, followed magnesium Stearate.
B) Controlled Release Component: Tapentadol HCl, HPMC K100M Premium CR, lactose monohydrate and microcrystalline cellulose were sifted through suitable sieve (40 #SS), mixed well, followed by mixing with aerosil and magnesium stearate.
C) Delayed Controlled Release Component: Tapentadol HCl, eudragit L100, lactose monohydrate, microcrystalline cellulose, HPMC K100M Premium CR, HPMC K100 LVCR were sifted and mixed well, followed by mixing with aerosil and magnesium stearate.
D) The delayed controlled release component blend was compressed followed by immediate release component blend and finally controlled release component blend using 13.3 mm round shape punch to prepare a trilayer tablet with hardness 250-300 N, and thickness 7.8-8.4 mm.

Manufacturing Procedure of Example 19:
A) Immediate Release Component: Same as Example 18.
B) Controlled Release Component: Tapentadol HCl, lactose monohydrate, a part of microcrystalline cellulose and croscarmellose sodium were sifted, mixed well and granulated with a solution of PVP in sufficient quantity of water. The granules were dried, sized and mixed with sifted HPMC K100M Premium CR and Aerosil 200 and finally lubricated with magnesium stearate.

C) Delayed Controlled Release Component: Tapentadol HCl, lactose monohydrate and microcrystalline cellulose and, a part of croscarmellose sodium were sifted, mixed well and granulated with a solution of PVP in sufficient quantity of water. The granules were dried, sized and mixed with sifted eudragit L100, HPMC K100M Premium CR and HPMC K100 LVCR and finally lubricated with magnesium stearate.
D) The tablets were prepared like example 18.

Manufacturing Procedure of Example 20:
A) Immediate Release Component: Same as Example 18.
B) Controlled Release Component: Same as Example 19, except HPMC K100 LVCR was mixed along with HPMC K100M Premium CR and Aerosil 200 with the drug granules.
C) Delayed Controlled Release Component: Same as Example 19, except eudragit L100 was additionally mixed with Tapentadol HCl, lactose monohydrate, microcrystalline cellulose and, a part of croscarmellose sodium to prepare granules using PVP K30 solution.
D) The tablets were prepared like example 18.

Manufacturing Procedure of Example 21:
A) Immediate Release Component: Same as Example 18.
B) Controlled Release Component: Hydrogenated Vegetable oil was sifted through suitable Sieve (20 #SS), melted and first PEG 6000 followed by tapentadol, lactose monohydrate and microcrystalline cellulose was added to the melted mass with stirring. The melted mass was cooled, sized and mixed with sifted HPMC K100M Premium CR and Aerosil 200. Finally the above blend was lubricated with magnesium stearate.
C) Delayed Controlled Release Component: Same as Example 20.
D) The tablets were prepared like example 18.

EXAMPLE 22

Tapentadol Immediate Release (IR) 75 mg Tablet

| Ingredients | % w/w of ingredients |
|---|---|
| Tapentadol HCl equivalent to Tapentadol 75 mg | 33.0 |
| Lactose Monohydrate | 29.7 |
| Microcrystalline Cellulose | 30.1 |
| Croscarmellose Sodium | 2.8 |
| Polyvinyl pyrrolidone | 3.8 |
| Purified Water | q.s. |
| Magnesium Stearate | 0.6 |
| Film Coat (3% w/w) | |
| Opadry Pink | 3.0 |
| Purified Water | q.s. |

Manufacturing Procedure: Tapentadol HCl, lactose monohydrate, a part of microcrystalline cellulose and croscarmellose sodium were sifted through suitable sieve (40#S.S), mixed well and granulated with solution of polyvinyl pyrrolidone in purified water. The granules were dried, sized and mixed with remaining part of sifted microcrystalline cellulose and croscarmellose sodium. The above blend was lubricated with magnesium stearate and compressed using round shape 8.5 mm round shape punch plain on both side with suitable physical parameters. The compressed tablets were further coated with opadry pink in purified water to 3% w/w weight gain of the total weight of the tablet.

Swelling of the tablets as prepared in example 4 was measured by placing the tablets in 900 ml 0.1 N HCl USP type II (paddle type) apparatus at 37° C. and 100 rpm. At different time intervals, tablets from each dissolution vessel were taken out and placed on cellophane paper. Excess of the media was blotted off and the dimensions of the tablets were measured using calibrated Vernier calipers. The swelling data for the example 4 is as given below:

| Time in Hours | Average diameter (mm) |
|---|---|
| 0 | 13.3 |
| 0.5 | 14.5 |
| 1 | 15.3 |
| 2 | 15.6 |
| 4 | 15.9 |
| 6 | 16.1 |
| 16 | 19.3 |

Dose dumping test was conducted under following conditions: Media: 0.1 N HCl, 900 ml & 0.1N HCl containing 20% v/v Ethanol, 900 ml; Method: USP-1,100 RPM; Time Point: 15, 30, 45, 60, 90, 120 min.

Dissolution Data:

| | Example 20 | | Example 21 | |
|---|---|---|---|---|
| Time (min) | % of tapentadol released in 0.1N HCl | % of tapentadol released in 0.1N HCl containing 20% v/v alcohol | % of tapentadol released in 0.1N HCl | % of tapentadol released in 0.1N HCl containing 20% v/v alcohol |
| 0 | 0 | 0.0 | 0.0 | 0 |
| 15 | 8 | 5.4 | 7.9 | 6.7 |
| 30 | 12.8 | 8.7 | 11.9 | 10.2 |
| 45 | 15.9 | 11.2 | 15.6 | 13.1 |
| 60 | 20.7 | 13.5 | 20.4 | 15.7 |
| 90 | 26.5 | 17.6 | 24.4 | 20.3 |
| 120 | 33.7 | 22.0 | 30.0 | 24.6 |

The dissolution of composition of examples 20 and 21 in 0.1 N HCl and 0.1N HCl containing 20% v/v alcohol shows that tapentadol dissolve slowly in alcohol containing media as compared to 0.1 N HCl and hence there is no dose dumping of tapentadol from the controlled release pharmaceutical composition.

In a monocentric two-way crossover study, open label, randomized clinical trial, the compositions of example 19 as a single tabletted dose of 300 mg tapentadol was administered once daily (QD) as test and a tapentadol immediate release formulation of dose 75 mg (example 22) which was administered four times daily (QID) as reference, were administered to four healthy volunteers in fed state, to determine pharmacokinetic data. The test tablets were administered at 0 hours and reference tablets were administered at 0, 6, 12 and 18 hours. Data was determined experimentally by HPLC analysis.

| Reference (Ref) | | Test (Example 19) | | |
|---|---|---|---|---|
| $AUC_{last}$ [ng · hr/ml] | $C_{max}$ [ng/ml] | $AUC_{last}$ [ng · hr/ml] | $C_{max}$ [ng/ml] | $C_{24\ hr}$ [ng/ml] |
| 2239.74 | 155.57 | 2132.16 | 134.71 | 49.00 |

In a monocentric, open label, randomized, three-treatment, three-period, three-sequence, crossover oral clinical trial, the compositions of examples 20 and 21 as a single tabletted dose of 300 mg tapentadol were administered once daily (QD) as Test 1 & Test 2 respectively and a commercially available tapentadol immediate release formulation of dose 75 mg (Nucynta®) which was administered four times daily (QID) as reference, were administered to fifteen healthy volunteers in fed state, to determine pharmacokinetic data. The test tablets were administered at 0 hours and reference tablets were administered at 0, 6, 12 and 18 hours. Data was determined experimentally by HPLC analysis.

The essential pharmacokinetic data are shown in the following table.

| Reference (Ref) | | Test 1 (Example 20) | | | Test 2 (Example 21) | | |
|---|---|---|---|---|---|---|---|
| $AUC_{last}$ [ng·hr/ml] | $C_{max}$ [ng/ml] | $AUC_{last}$ [ng·hr/ml] | $C_{max}$ [ng/ml] | $C_{24\ hr}$ [ng/ml] | $AUC_{last}$ [ng·hr/ml] | $C_{max}$ [ng/ml] | $C_{24\ hr}$ [ng/ml] |
| 2462.739 | 170.981 | 2193.409 | 162.467 | 32.246 | 2082.682 | 175.740 | 23.374 |

$C_{24\ hr}$: Serum concentration of tapentadol at 24 hours after administration of controlled release composition.

The invention claimed is:

1. A controlled release pharmaceutical composition comprising: an immediate release component comprises about 4% to about 12% of tapentadol a delayed release component comprises about 32% to about 84% of tapentadol, and a controlled release component comprises about 18% to about 65% of tapentadol by weight of total weight of tapentadol in the composition, wherein the composition is gastroretentive and maintains serum concentration of tapentadol of at least 20 ng/ml for at least 17 hours after once daily oral administration of the composition.

2. The controlled release pharmaceutical composition of claim 1, wherein the composition is multilayered.

3. The controlled release pharmaceutical composition of claim 2, wherein the composition is trilayered comprising first, second and third layer wherein the first layer comprises controlled release component, second layer comprises immediate release component and the third layer comprises delayed release component.

4. The controlled release pharmaceutical composition of claim 3, wherein immediate release component, a controlled release component, and a delayed release component comprises tapentadol.

5. The controlled release pharmaceutical composition of the claim 1, wherein the pharmaceutical composition maintains at least 10 ng/ml serum concentration of tapentadol for at least 14 hours after administration.

6. The controlled release pharmaceutical compositions of claim 1 further comprise one or more active ingredients.

7. The controlled release pharmaceutical compositions of claim 1, wherein the composition is used for the treatment of pain.

* * * * *